United States Patent [19]

Meijer

[11] 4,166,454

[45] Sep. 4, 1979

[54] CARDIAC MONITOR

[76] Inventor: Robert Meijer, 3117 D. N. Orchard St., Chicago, Ill. 60657

[21] Appl. No.: 769,705

[22] Filed: Feb. 17, 1977

[51] Int. Cl.² ............................................. A61B 5/02
[52] U.S. Cl. ................................. 128/666; 128/664; 128/689
[58] Field of Search ...................... 128/2.05 A, 2.05 V, 128/2 L, 2.05 F, 2.05 R, 2.05 T, 2.05 P

[56] References Cited

U.S. PATENT DOCUMENTS

| | | | |
|---|---|---|---|
| 3,463,142 | 8/1969 | Harte | 128/2 L |
| 3,841,314 | 10/1974 | Page | 128/2 L |
| 3,858,574 | 1/1975 | Page | 128/2.05 T |
| 3,980,075 | 9/1976 | Heule | 128/2.05 V |
| 4,063,551 | 12/1977 | Sweeney | 128/2.05 P |

*Primary Examiner*—Dalton L. Truluck
*Assistant Examiner*—Francis J. Jaworski

*Attorney, Agent, or Firm*—Silverman, Cass & Singer, Ltd.

[57] ABSTRACT

A cardiac monitor generates infrared light which is directed at the skin of an individual to be monitored. The light reflected from the skin is detected and automatically controlled. The pulsatile flow of blood in the underlying vascular network modulates the reflected light which is detected by a photo sensitive sensor which generates a signal indicative of the modulations. The modulated signal is coupled to a pulse detector which filters our spurious signals and generates one pulse for each systole in a cardiac cycle. The systolic pulse is coupled to a pulse interval to heartbeat rate converter which converts the interval between each succeeding systolic pulse into a signal which is preferably continuously and visually displayed to provide a continuous monitor of the heartbeat rate of the monitored individual.

14 Claims, 3 Drawing Figures

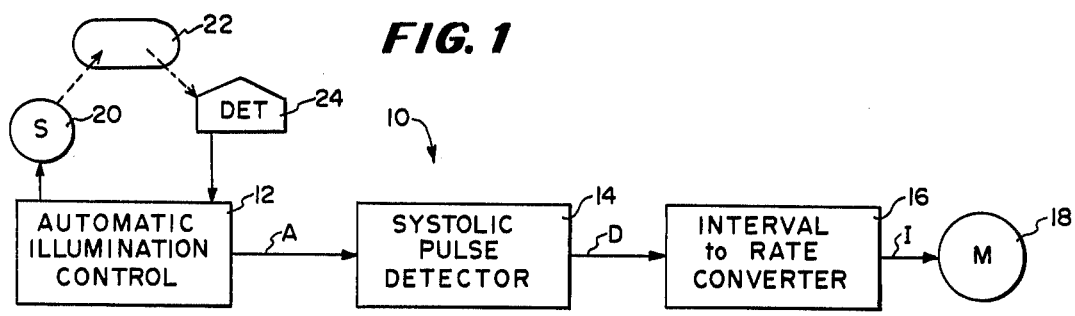
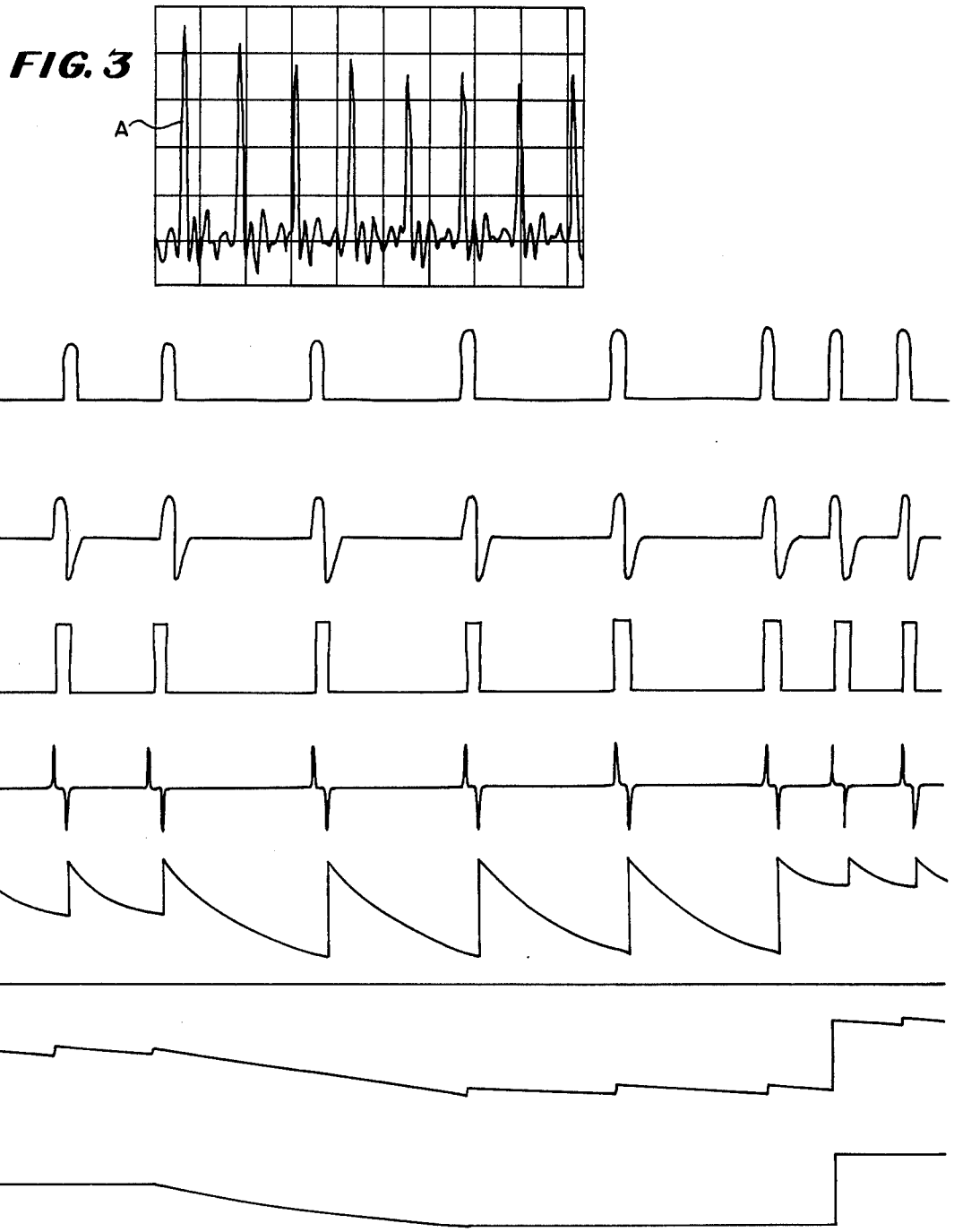

CARDIAC MONITOR

BACKGROUND OF THE INVENTION

The invention relates to a cardiac monitor for monitoring the pulsatile flow of blood through the vascular network under the skin of a person and more particularly to a cardiac monitor which monitors reflected light modulated by the pulsatile flow of blood.

The characteristics of individual heartbeats within a single cardiac cycle and the rate of the individual heartbeats have long been recognized as significant indicators of over-all physiological status of the person. The most rudimentary monitoring methods required that the physician sense the cardiac rhythm by acoustic methods or by physically contacting the skin to feel the pulses. The physician was then required to note the differences between the activity he heard or felt and "normal" activity. Information on the rate of heartbeats was only attainable by actually counting the number of cardiac cycles occurring within a predetermined period of time.

Recent advances in electrocardiography have allowed the cardiac activity to be monitored as tiny fluctuations in the electrical potentials between various parts of the body. A drawback of this method is that the small magnitude of these potentials, the presence of muscular artifacts, the requirement for intimate electrical contact as well as the danger of an electrical shock to the person makes this method relatively expensive, cumbersome and of limited utility. Other methods have been attempted including ultrasonic and magnetic equipment, but these methods are seldom used due to their complexity.

The need has developed for a cardiac monitor which may be operated by the individual being monitored such as surviving heart attack victims, potential heart attack victims or physicians themselves. Another need exists for individuals wishing to optimize their physical activities by maintaining an optimum rate of cardiac activity during exercise.

One solution suggested to overcome the problems of the prior art is the use of optical sensing of the biological functions; however, these prior art optical sensing systems also have not provided a convenient, economical and lightweight unit which conveniently allows the individual to obtain rate information normally obtainable from E.C.G. equipment. Furthermore, these systems do not provide a fast and non-complex method of obtaining the heartbeat rate.

SUMMARY OF THE INVENTION

The above and other disadvantages of prior art cardiac monitoring devices and techniques are overcome in accordance with the present invention by providing a compact, economical and portable cardiac monitor which generates light and monitors the reflected light modulations from the pulsatile flow of blood beneath the skin of the individual being monitored. The monitor includes an automatic illumination control to automatically adjust the nominal light intensity to compensate for variations in the sensor location and skin tone. The systolic pulses are detected by a systolic pulse detector which filters out spurious signals in the cardiac cycle. Once the systolic pulses have been detected, the interval between each two successive systolic pulses is utilized to determine the heartbeat rate by converting the pulse intervals to a steady heartbeat rate signal. Thus, the monitor generates a continuous output signal proportional to the rate of the heartbeats, which signal is updated by each subsequent systolic pulse.

BRIEF DESCRIPTION OF THE DRAWINGS

FIG. 1 is a block diagram of the cardiac monitor;

FIG. 3 is a chart of the signal waveforms generated in the cardiac monitor.

DESCRIPTION OF THE PREFERRED EMBODIMENT

Figure 2:
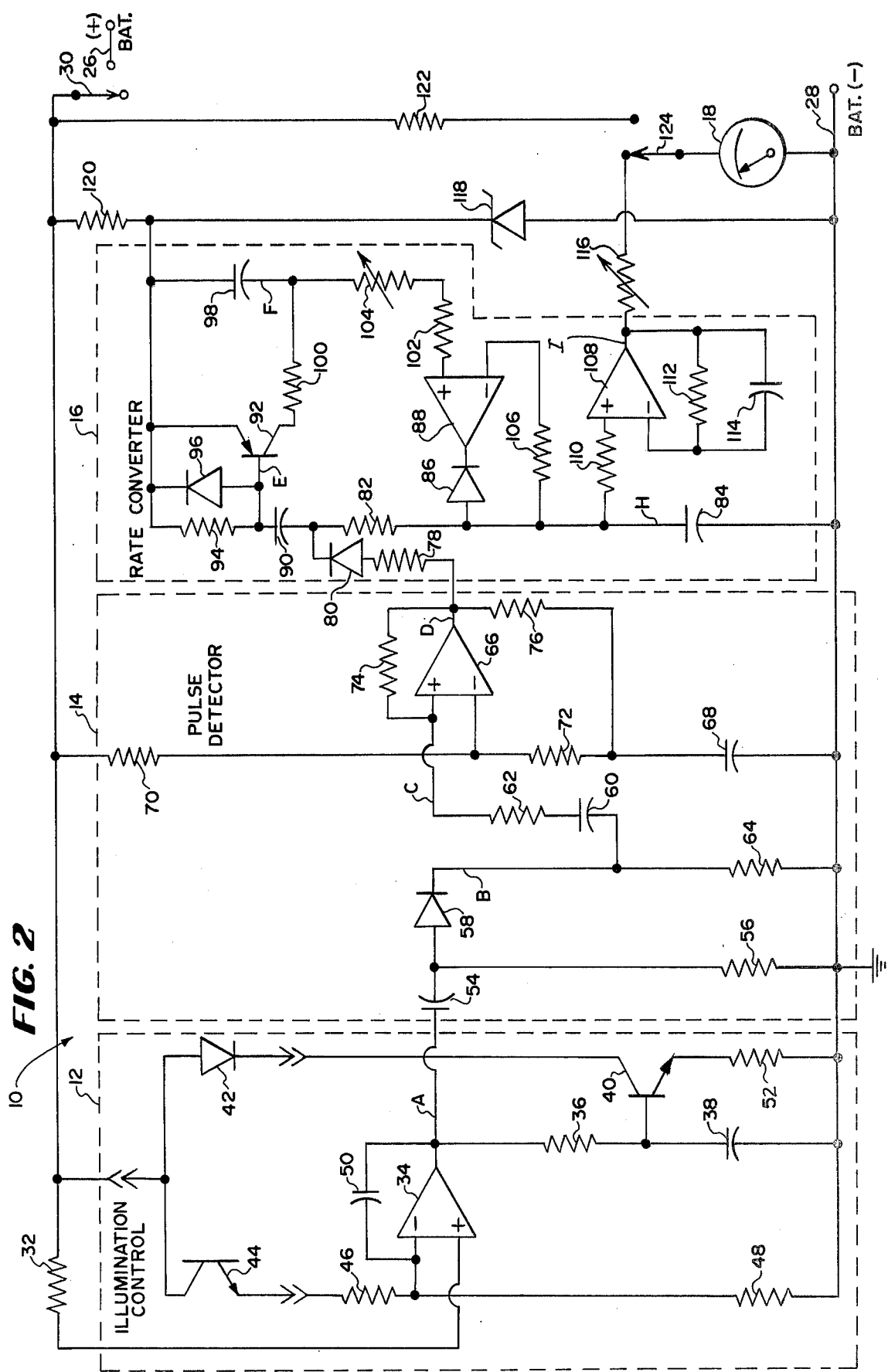
FIG. 2 is a schematic diagram of the cardiac monitor.

As indicated above, the invention is concerned with a cardiac monitor for monitoring the pulsatile flow of blood in an individual by monitoring light reflected from the vascular network of the individual. The nominal illumination intensity is automatically adjusted to maintain a substantially constant level of reflected light at the photo sensor. The systolic pulses are detected and converted to a signal indicative of the heartbeat rate to provide a continuous output signal proportional to the heartbeat rate.

Referring now to FIG. 1, the cardiac monitor of the invention is designated generally at 10 which comprises an automatic illumination control 12 which is coupled to a systolic pulse detector 14 which is in turn coupled to an interval-to-rate converter 16 which generates an output signal displayed on a meter 18. In operation, the illumination control 12 activates a light source 20 which generates the light directed at a portion of skin 22 of an individual to be monitored. The light most preferably is in the infrared range (wavelength of 0.75 to 1000 microns) and the reflection of the light from the skin portion 22 is detected by a light detector or photo sensor 24. The light detector 24 generates a signal A (FIG. 3) indicative of the light reflected from the underlying vascular network of the skin portion 22. The signal A is modulated by the pulsatile flow of blood and is coupled through the control 12 to the systolic pulse detector 14. The systolic pulse detector 14 in turn substantially eliminates all components except the systolic pulses and produces a positive signal pulse D indicative only of each systolic pulse which is coupled to the rate converter 16. The rate converter 16 in turn generates a continuous signal I directly proportional to the interval between each systolic pulse which is in turn directly related to the heartbeat rate which is sought after and coupled to the meter 18 for display.

Connection to the body skin portion 22 may be made at any point where a reasonable amount of vascularization is near to the skin surface. Examples include the balls of the fingers or toes, and the ear lobes. Experimentation has shown that areas of the skin that blanch easily with pressure are best utilized.

The details of the monitor 10 are best illustrated in FIG. 2. Electrical power is supplied to the monitor 10 from a battery (not shown) or other direct current power source through a positive terminal 26 and a negative terminal 28. To operate the monitor 10 a switch 30 is connected to the positive terminal 26 supplying a reference current through a resistor 32 to the illumination control 12 as well as to the other circuit elements of the monitor 10.

The current through resistor 32 is coupled to the positive input of a first current amplifier 34. The output signal A from the amplifier 34 is determined by the difference in magnitude between the positive and negative input currents to the amplifier inputs. Immediately after the switch 30 is connected to the battery a fixed current flows into the positive input of the amplifier 34 and the output of the amplifier 34 will in turn be driven to its maximum positive signal output. This positive output is coupled through a resistor 36 to a capacitor 38. The current through the resistor 36 charges the capacitor 38 with a positive charge. The positive voltage on the capacitor 38 supplies the base drive to a transistor 40. The transistor 40 in turn is coupled to a light emitting diode (LED) 42. As the base drive or signal to the transistor 40 becomes more positive the current supply to the LED 42 increases and the light intensity emitted from the LED 42 will increase until the nominal phototransistor current value is achieved.

As previously mentioned, the light from the LED 42 is preferably in the infrared range and is directed to a portion of the skin of the individual to be monitored. The modulated illumination reflected from the individual is detected by a phototransistor 44. The average intensity of the illumination is directly proportional to the current generated by the transistor 44 which is coupled through a limiting resistor 46 into the negative input of the amplifier 34. The current limiting resistor 46 protects the amplifier 34 from very intense illumination levels. A portion of the current from the phototransistor 44 is diverted to ground through a resistor 48, because the current from the transistor 44 is larger than the optimum current input for the negative terminal of the amplifier 34.

Illumination of the phototransistor 44 from the LED 42 is automatically maintained at a proper average illumination level by virtue of the slow negative feedback path via the optical path of the amplifier 34. The resistor 36 and the capacitor 38 are chosen to filter out the rapid changing signal components caused by the pulsatile flow of the blood from the negative feedback path so that rapid changes in illumination on the transistor 44 result in the signal A being amplified by essentially the full open loop gain of the amplifier 34. A small capacitor 50 is coupled from the output of the amplifier 34 to the negative input to filter out interference of a frequency significantly higher than the modulation of interest. The relationship between current output from the transistor 40 and the voltage applied to the base of the transistor is established by a resistor 52.

Hence, the nominal or average illumination on the transistor 44, via reflected light, is maintained at a constant level. The resistor 36 and the capacitor 38 provide the negative feedback to maintain the average intensity level. The very rapid changes, beyond the frequency of interest, are ignored through the action of the capacitor 50. Thus illumination variations of interest are selectively amplified by the amplifier 34, as shown by the signal A.

The signal A (FIG. 3) generated by the amplifier 34 reflects the complete cardiac activity of the individual being monitored. The changes in the reflected light into the phototransistor 44 due to cardiac activity are relatively rapid and are amplified essentially by the open loop gain of the amplifier 34. Slow changes in the reflected light intensity due to body movement and other non-cardiac activity result in corresponding changes in the current generated by the transistor 40 which is part of the negative feedback path of the amplifier 34. The net effect is that the rapid changes in the light reflected from the cardiac activity in the vascular network are highly amplified while the slow changes undergo negligible amplification as can be seen by the waveform A where the most positive pulses are the systolic pulses.

The small ripples in the waveform A are significant parts of the cardiac cycle and are other accurate indications of the heart's activity. With appropriate display or recording equipment these parts of the cardiac cycle may also be utilized. The full scale output of the amplifier 34 takes place with a very small variation in the illumination. If the average or nominal illumination is allowed to increase too high, the amplifier 34 will saturate and no usable signal will be generated. Part of the function of the illumination control 12 is to maintain the average illumination level within the linear, non-saturated region of the amplifier 34. The gradual drop in the level of the systolic peaks in the waveform A illustrates how the effect of large, but slow, changes in the illumination level caused by movement, breathing, etc. is minimized.

To distinguish the peak systolic positive pulse from the other pulses as shown in the waveform A the output of the detector 34 is coupled into the pulse detector 14. When a systolic pulse occurs the positive going portion of the pulse or signal charges a capacitor 54 to the peak positive value of the pulse. During the balance of the negative going pulse portion the capacitor 54 retains its charge with the output of the capacitor driven to a below ground potential because of a resistance 56 which has a substantially larger impedance than the output impedance of the amplifier 34. During the time period between the systolic pulses the negative or output side of the capacitor 54 slowly approaches toward ground potential as current flows through the resistor 56. When the next positive systolic pulse occurs the current will flow into a diode 58 only if the magnitude of the next occurring systolic pulse appearing at the output of the amplifier 34 is larger than the voltage charge stored on the capacitor 54. In this manner, each systolic pulse must be of a magnitude approximately equal to the magnitude of the previous systolic pulse to ensure the forward biasing of the diode 58. Thus all other components occurring between the systolic pulses will be filtered from the signal as shown by the waveform A.

Each systolic pulse will then forward bias the diode 58 producing a short positive output pulse as indicated by the waveform B. The output pulse from the diode 58 is in turn differentiated by a capacitor 60 and a resistor 62 to produce a current pulse as shown by the waveform C. The function of the diode 58, the capacitor 60, the resistor 62 and a second resistor 64 is to provide a high pass filter to minimize sensitivity to changes in illumination caused by non-systolic components of the signal A. The high pass filter is utilized to keep the pulse detector 14 from responding to signals other than the systolic pulses.

The pulse from the filter is coupled to the positive input of an amplifier 66. The amplifier 66 is connected as a typical one shot multivibrator which will generate a positive output pulse of definite duration and magnitude once during each systolic pulse as can be seen by the waveform D. The other conventional elements of the multivibrator are a capacitor 68 and resistors 70, 72, 74 and 76. The capacitor 68 in conjunction with the resistor 76 determines the length of the positive output pulses from the amplifier 66. The resistor 76 couples the output of the amplifier 66 to the timing capacitor 68 to establish a delayed negative feedback for normal monostable multivibrator operation. The resistor 70 determines the threshold level to trigger the multivibrator while the resistor 72 limits the current into the negative terminal of the amplifier 66. The resistor 74 provides the positive feedback for the amplifier 66.

The positive pulses indicative of the systolic pulses generated by the amplifier 66 are coupled to the pulse interval to rate converter 16 to be converted to an output corresponding to the heartbeat rate. The positive pulse produced by the amplifier 66 is coupled through a current limiting resistor 78, forward biasing a diode 80 through a resistor 82 to charge a capacitor 84. The capacitor 84 is positively charged until its voltage level forward biases a diode 86. The charge on the capacitor 84 is shown by the waveform H. The waveform G illustrates the maximum voltage which can appear on the capacitor 84, with regard to waveform H, due to the regulating action of a zener diode 118.

Once the diode 86 becomes forward biased the capacitor 84 is clamped at a charge level determined by the voltage level at the output of an amplifier 88 which is determined by the instantaneous charge level on a capacitor 98 at the occurrence of the positive pulse D. When the output pulse from the amplifier 66 terminates and recedes to its quiescent value a negative going pulse is coupled through a capacitor 90 to the base of a transistor 92. A resistor 94 is coupled to the base of the transistor 92 to ensure that the transistor 92 remains off when base drive is not present. A diode 96 is also coupled to the base of the transistor 92 to prevent the transistor 92 base from being reverse biased when the output of the amplifier 66 goes positive. The diode 96 is a conventional diode; however, it could be replaced by a LED to generate a visible light flash for each heartbeat.

The negative going pulse coupled to the base of the transistor 92 will cause the capacitor 98 to discharge through a limiting resistor 100 as shown by the waveform F. Hence, immediately after a systolic positive pulse occurs essentially zero volts appear across the capacitor 98.

In the interval between the systolic pulses the capacitor 98 will negatively charge from a current through resistors 102 and 104. When the next systolic pulse occurs, the output voltage of the amplifier 88 is at a level determined by the elapsed time between the last two systolic pulses. This output of the amplifier 88 determines the clamping level for the capacitor 84.

The selection of the capacitor 98 and the resistor 102 as well as the selection and setting of the resistor 104 determine the portion of the current versus time curve to be utilized and hence the linearity of the meter 18 readout. Preferably the components are chosen so that the meter may have a suppressed zero reading so that some minimum voltage level corresponds to a zero meter reading. A second much larger voltage level corresponds to a full scale meter reading. By choosing the correct values of the components the meter scale will be essentially linear and have a suppressed zero. Different scale shapes and meter ranges are easily attainable with different degrees of zero suppression on the meter with correspondingly different values of the components chosen. If a preprinted meter scale is utilized then the resistor 104 is adjusted to assure that the meter is properly calibrated. For example, in utilizing a 0 to 500 micro ampere meter with the capacitor 98 having a value of one microfarad, the resistor 102 having a value of 300K ohms and the potentiometer 104 having a value of 100K ohms, the relationship between the meter reading and pulse rate is indicated in Table 1:

TABLE 1

| Heartbeats per minute | *Meter Current | % Scale | Heartbeats per minute | *Meter Current | % Scale |
|---|---|---|---|---|---|
| 50 | 17.626 | 0 | 155 | 282.126 | 52.9 |
| 55 | 22.786 | 1.032 | 160 | 296.458 | 55.766 |
| 60 | 29.329 | 2.341 | 165 | 310.604 | 58.596 |
| 65 | 37.207 | 3.916 | 170 | 324.554 | 61.386 |
| 70 | 46.328 | 5.740 | 175 | 338.296 | 64.134 |
| 75 | 56.572 | 7.789 | 180 | 351.824 | 66.840 |
| 80 | 67.805 | 10.036 | 185 | 365.131 | 69.501 |
| 85 | 79.893 | 12.453 | 190 | 378.214 | 72.118 |
| 90 | 92.701 | 15.015 | 195 | 391.069 | 74.689 |
| 95 | 106.105 | 17.696 | 200 | 403.696 | 77.214 |
| 100 | 119.991 | 20.473 | 205 | 416.094 | 79.694 |
| 105 | 134.255 | 23.326 | 210 | 428.263 | 82.127 |
| 110 | 148.805 | 26.236 | 215 | 440.205 | 84.516 |
| 115 | 163.558 | 29.186 | 220 | 451.921 | 86.859 |
| 120 | 178.443 | 32.163 | 225 | 463.413 | 89.157 |
| 125 | 193.399 | 35.155 | 230 | 474.685 | 91.412 |
| 130 | 208.373 | 38.149 | 235 | 485.738 | 93.622 |
| 135 | 223.318 | 41.138 | 240 | 496.577 | 95.790 |
| 140 | 238.196 | 44.114 | 245 | 507.205 | 97.916 |
| 145 | 252.975 | 47.070 | 250 | 517.626 | 100.00 |
| 150 | 267.626 | 50.00 | | | |

*micro ampere

A negative feedback resistor 106 is coupled to the negative input of the amplifier 88 to establish unity gain.

As can be seen from the waveform F the output of the amplifier 88 at the moment a systolic pulse occurs will be large or smaller depending upon the interval between the systolic pulses. If the interval between systolic pulses is larger than the previous interval the capacitor 84 will be clamped at a lower level. If the interval is shorter than the previous interval the capacitor 84 will be clamped at a higher level than the previous voltage level. This is clearly indicated by the waveform F and the waveform H in FIG. 3.

The net result is that the voltage level on the capacitor 84 is proportional to the rate at which the heart is beating. The relationship between the rate at which the heart is beating and the voltage level on the capacitor 84 is approximately linear with the proper choice of the capacitor 98 and the resistors 102 and 104, as previously mentioned. A sudden change in the heartbeat rate, indicated as a sudden change in the interval, will produce an immediate corresponding change in the voltage level on the capacitor 84 as indicated by the waveform H. As long as the heartbeat rate remains relatively steady the voltage level on the capacitor 84 will remain essentially constant. The monitor 10 thus provides an output as indicated by the charge level on the capacitor 84 which is proportional to the heartbeat rate which is updated on each subsequent systolic pulse.

The charge level on the capacitor 84 is coupled to the meter 18 by a buffer amplifier 108. The amplifier 108 input is coupled to the capacitor 84 through a resistor 110. The gain of the amplifier 108 is set by a resistor 112 in conjunction with the resistor 110 while a capacitor 114 limits the response speed of the amplifier 108 to the voltage level changes on the capacitor 84. The output of the amplifier 108 is indicated by the waveform I which is coupled through a potentiometer to the meter 18. The potentiometer 116 is varied to set the span of the meter 18.

The zener diode 118 in series with a resistor 120 regulates the rate converter 16 to eliminate sensitivity to fluctuations in the power supply. A resistor 122 is coupled to the power supply input to provide a battery test by utilizing a switch 124 to couple the resistor 122 to the meter 18 to provide a visual indication of the power supply status.

Immediately after a systolic pulse the pulse detector 14 will not accept any pulse with an amplitude smaller than the systolic pulse which just occurred, as previously discussed. As time lapses, the capacitor 54 slowly discharges which lowers the threshold level necessary to trigger the detector 14. The variable threshold level established is generally ideal for detecting the systolic pulses as the magnitude of the systolic pulse peaks in waveform A will decrease as the rate slows down.

In the event of a stopped heart the waveforms A, B, C, D and E will become zero or flat immediately. Waveform F starts at its peak positive value after the last systole and slowly decays to zero. As soon as the voltage F drops below the voltage previously left on the capacitor 84, the diode 86 becomes forward biased and the voltage on the capacitor 84 is pulled down, tracking the decaying voltage F. The components are chosen such that the transition from the diode 86 being back biased to forward biased takes place after a time interval equal to the previous time interval between heartbeats. The amplifier 88 can only clamp or decrease the voltage on the capacitor 84. The only way to increase the voltage on the capacitor 84 is via the positive pulse D from the amplifier 66.

As described, the continuously updated heart rate is not totally equivalent to an E.C.G.; however, the waveform A contains sufficient information to be equivalent to an E.C.G. The particular diagnostic value of the beat by beat rate information is in its indication of:

A. Arrhythmias
B. Pain and emotional distress
C. Valsalvas Maneuver
D. Brain damage.

The non-diagnostic value of the rate information include:

E. Exercise optimization
F. Bio feedback.

The invention is valuable in saving time for nurses and others as it eliminates the long wait associated with manually counting pulses utilizing a watch or clock for a predetermined time period. The invention is sufficiently sensitive to clearly display otherwise inperceptible arrhythmias without the use of the expensive, difficult to interpret and generally non-portable E.C.G. equipment.

The representative component values for one specific embodiment of the monitor are listed in Table 2.

TABLE 2*

| COMPONENT | VALUE OR TYPE | COMPONENT | VALUE OR TYPE |
| --- | --- | --- | --- |
| 32 | 1 Meg | 78 | 120 |
| 34 | LM3900 | 80 | IN914 |
| 36 | 100K | 82 | 15K |
| 38 | 100uf | 84 | 100uf |
| 40 | 2N5306 | 86 | IN914 |
| 42 | TIXL | 88 | LM3900 |
| 44 | TIL | 90 | .047uf |
| 46 | 2.2K | 92 | 2N3645 |
| 48 | 3.9K | 94 | 68K |
| 50 | 4000pf | 96 | IN914 |
| 52 | 220 | 98 | 1.0uf |
| 54 | 1.0uf | 100 | 330 |
| 56 | 10M | 102 | 300K |
| 58 | IN914 | 104 | 100K |
| 60 | .01uf | 106 | 390K |
| 62 | 2.2K | 108 | LM3900 |
| 64 | 1M | 110 | 1M |
| 66 | LM3900 | 112 | 1M |
| 68 | .22uf | 114 | 1.0uf |
| 70 | 10M | 116 | 50K |
| 72 | 1M | 118 | IN821 |
| 74 | 3M | 120 | 820 |
| 76 | 1M | 122 | 47K |

*All resistance in ohms
uf = micro farad
pf = pico farad

Many modifications and variations of the present invention are possible in light of the above teachings. It is therefore to be understood that within the scope of the appended claims the invention may be practiced otherwise than as specifically described.

What is claimed and desired to be secured by Letters Patent of the United States is:

1. A method of monitoring cardiac activity including directing light at the skin of the individual to be monitored and detecting the reflected light modulated by the pulsatile flow of blood beneath the skin, said method including:
   detecting substantially the peak of the systolic pulse in the cardiac cycle, including automatically coupling a signal indicative of the reflected light into a filtering means, storing a charge level indicative of the peak of said reflected light signal in said filtering means, comparing each signal pulse occurring in said reflected light to said stored charge level, and generating a pulse indicative of each systolic pulse only when a succeeding signal pulse has a peak substantially equal to said charge level;
   generating a signal indicative of each detected pulse peak; and
   converting the time interval between signals to a signal indicative of the heartbeat rate.

2. A method of monitoring as claimed in claim 1 further including:
   automatically controlling the intensity of the light reflected from the skin.

3. A method of monitoring as claimed in claim 2 wherein automatically controlling the intensity of the light reflected from the skin includes:
   coupling the detected reflected light to an amplifying means;
   generating a signal output from said amplifying means which is coupled to means for generating and directing light at the skin; and
   utilizing a portion of said amplifying means signal to automatically compensate for non-cardiac activity interference in the intensity of the reflected light.

4. A method of monitoring cardiac activity including directing light at the skin of the individual to be monitored and detecting the reflected light modulated by the pulsatile flow of blood beneath the skin, said method including:
   detecting substantially the peak of the systolic pulse in the cardiac cycle;
   generating a signal indicative of each detected pulse peak; and
   converting the time interval between signals to a signal indicative of the heartbeat rate, including discharging a charge storage means in response to each signal, charging said storage means at a predetermined rate between signals, charging a second storage means to a level indicative of the charge on said first storage means when each signal occurs, clamping said second storage means at said indicative level between signals, and generating a rate signal corresponding to the clamped level of said second storage means.

5. A method of monitoring as claimed in claim 4 wherein detecting each systolic pulse includes:
 coupling a signal indicative of the reflected light into a filtering means;
 storing a charge level indicative of the peak of said reflected light signal in said filtering means;
 comparing each signal pulse occurring in said reflected light to said stored charge level; and
 generating a pulse indicative of each systolic pulse only when a succeeding signal pulse has a peak substantially equal to said charge level.

6. A method of monitoring as claimed in claim 5 further including:
 automatically controlling the intensity of the light reflected from the skin.

7. A method of monitoring as claimed in claim 6, wherein automatically controlling the intensity of the light reflected from the skin includes:
 coupling the detected reflected light to an amplifying means;
 generating a signal output from said amplifying means which is coupled to means for generating and directing light at the skin; and
 utilizing a portion of said amplifying means signal to automatically compensate for non-cardiac activity interference in the intensity of the reflected light.

8. A cardiac monitor for monitoring cardiac activity including means for generating and directing light at the skin of the individual to be monitored and means for detecting the reflected light modulated by the pulsatile flow of blood beneath the skin, said monitor including:
 means for detecting substantially the peak of the systolic pulse in the cardiac cycle, said detecting means including means for generating a signal indicative of the reflected light, means for automatically storing a charge level indicative of the peak of said reflected light signal, means for comparing each signal pulse occurring in said reflected light signal to said stored charge level, and means for generating a pulse indicative of each systolic pulse only when a succeeding signal pulse has a peak substantially equal to said charge level;
 means for generating a signal indicative of each detected pulse peak; and
 means for converting the time interval between signals to a signal indicative of the heartbeat rate.

9. A monitor as claimed in claim 8 further including:
 means for automatically controlling the intensity of the light reflected from the skin.

10. A monitor as claimed in claim 9 wherein said automatically controlling means include:
 means for coupling the detected reflected light to an amplifying means;
 means for generating a signal output from said amplifying means which is coupled to said means for generating and directing light at the skin; and
 feedback means for utilizing a portion of said amplifying means signal to automatically compensate for non-cardiac activity interference in the intensity of the reflected light.

11. A cardiac monitor for monitoring cardiac activity including means for generating and directing light at the skin of the individual to be monitored and means for detecting the reflected light modulated by the pulsatile flow of blood beneath the skin, said monitor including:
 means for detecting substantially the peak of the systolic pulse in the cardiac cycle;
 means for generating a signal indicative of each detected pulse peak; and
 means for converting the time interval between signals to a signal indicative of the heartbeat rate, said converting means including first charge storage means being discharged in response to each signal, means for charging said first storage means at a predetermined rate between signals, second storage means being charged to a level indicative of the charge on said first storage means when each signal occurs, means for clamping said second storage means at said indicative level between signals, and means for generating a rate signal corresponding to the clamped level of said second storage means.

12. A monitor as claimed in claim 11 wherein said systolic detecting means include:
 means for generating a signal indicative of the reflected light;
 means for storing a charge level indicative of the peak amplitude of said reflected light signal;
 means for comparing each signal pulse occurring in said reflected light signal to said stored charge level; and
 means for generating a pulse indicative of each systolic pulse only when a succeeding signal pulse has a peak substantially equal to said charge level.

13. A monitor as claimed in claim 12 further including:
 means for automatically controlling the intensity of the light reflected from the skin.

14. A monitor as claimed in claim 13 wherein said automatically controlling means include:
 means for coupling the detected reflected light to an amplifying means;
 means for generating a signal output from said amplifying means which is coupled to said means for generating and directing light at the skin; and
 feedback means for utilizing a portion of said amplifying means signal to automatically compensate for non-cardiac activity interference in the intensity of the reflected light.

* * * * *